United States Patent [19]

Park et al.

[11] Patent Number: 5,652,120
[45] Date of Patent: Jul. 29, 1997

[54] GENE CODING HUMAN EPIDERMAL GROWTH FACTOR AND PROCESS FOR PREPARING THE SAME

[75] Inventors: Seung Kook Park, Kyunggi-Do; Kang Moon Lee; Kyoo Seung Nho, both of Seoul; Yeo Wook Koh, Kyunggi-Do; Chang Hyuk Kwon, Seoul; Ju Young Chung, Seoul; Young Su Jee, Seoul; Young Hyo Yu, Kyunggi-Do, all of Rep. of Korea

[73] Assignee: Daewoong Pharmaceutical Co., Ltd., Kyunggi-Do, Rep. of Korea

[21] Appl. No.: 360,841

[22] PCT Filed: Apr. 25, 1994

[86] PCT No.: PCT/KR94/00036

§ 371 Date: Dec. 23, 1994

§ 102(e) Date: Dec. 23, 1994

[87] PCT Pub. No.: WO94/25592

PCT Pub. Date: Nov. 10, 1994

[30] Foreign Application Priority Data

Apr. 26, 1993 [KR] Rep. of Korea ............... 93-6978
Apr. 26, 1993 [KR] Rep. of Korea ............... 93-6979
Apr. 26, 1993 [KR] Rep. of Korea ............... 93-6980

[51] Int. Cl.$^6$ .................... C12N 15/18; C12N 1/21
[52] U.S. Cl. .............. 435/69.4; 435/252.3; 435/320.1; 530/399
[58] Field of Search ................. 435/69.4, 71.1, 435/240.1, 320.1; 530/300, 324; 536/23.1, 23.5, 23.51, 24.1

[56] References Cited

U.S. PATENT DOCUMENTS

| | | | |
|---|---|---|---|
| 4,743,679 | 5/1988 | Cohen et al. | 530/350 |
| 4,935,350 | 6/1990 | Patel et al. | 435/69.4 |
| 5,096,825 | 3/1992 | Barr et al. | 435/255 |
| 5,447,862 | 9/1995 | Heim et al. | 435/252.3 |

FOREIGN PATENT DOCUMENTS

| | | |
|---|---|---|
| 0 116 201 A1 | 8/1984 | European Pat. Off. . |
| 0 177 915 A2 | 4/1986 | European Pat. Off. . |
| 0 234 888 A2 | 9/1987 | European Pat. Off. . |
| 0 335 400 A2 | 10/1989 | European Pat. Off. . |
| 0335400A2 | 10/1989 | European Pat. Off. . |
| WO91/15228 | 10/1991 | WIPO . |

OTHER PUBLICATIONS

Ernst, J.F. Tibtech 6:196–199, 1988.
Fritsch, et al. Molecular Cloning, pp. 5.3–5.9, 17.20–17.24, 1987.
Carrier et al. Trends Biotech. 1:109–113, 1983.
Kim et al. Biotech. Prog. 9:548–554, 1993.
Wahle et al. EMBO J. 7:1889–1895, 1988.
Urdea, M.S. et al., Proc. Natl. Acad. Sci., USA 80:7461–7465, 1983.
Gregory, H. et al., Int. J. Peptide Protein Res. 9:107–118, 1977.
Sung, W.L. et al., Hybrid Gene Synthesis Approach, Nucleic Acids Research 14(15):6159–6168, 1986.

*Primary Examiner*—Vasu Jagannathan
*Assistant Examiner*—Christine Saoud
*Attorney, Agent, or Firm*—Darby & Darby

[57] ABSTRACT

The present invention relates to a novel gene coding human epidermal growth factor("hEGF") and a process for preparing the same employing a recombinant expression vector therefor. The hEGF gene of the invention is designed to contain codons ubiquitous in *E. coli* and the following restriction sites: HpaI at the 5' terminal, PstI at the 3' terminal and Bpu1102I, NsiI, MluI, Eco47III and AflII at a regular manner within its internal sequence. The present invention also provides a process for preparing hEGF by employing a expression vector pTE105 for hEGF, which contains expression cassette comprising Omp A leader sequence, translation termination sequence and transcription termination sequence and hEGF gene; and, replication origin of pUC19, tetracycline-resistant marker and a par site for stabilization in *E. coli*. The hEGF is produced massively in *E. coli* transformed with the pTE105(KCCM 10027).

3 Claims, 12 Drawing Sheets

FIG. 1

```
       Hpa I                              Bpu1102 I
5'   GTT AAC AGC GAC TCC GAA TGC CCG CTG AGC CAT GAC GGC TAC TGC CTG
3'   CAA TTG TCG CTG AGG CTT ACG GGC GAC TCG GTA CTG CCG ATG ACG GAC
      | N   S   D   S   E   C   P   L   S   H   D   G   Y   C   L
      └─────────────────►
       hEGF gene Nsi I                                         Mlu I
     CAC GAC GGC GTA TGC ATG TAC ATC GAA GCA CTG GAC AAA TAC GCG
     GTG CTG CCG CAT ACG TAC ATG TAG CTT CGT GAC CTG TTT ATG CGC
      H   D   G   V   C   M   Y   I   E   A   L   D   K   Y   A Eco47 III
     TGC AAC TGT GTT GTT GGC TAC ATC GGC GAG CGC TGT CAG TAC CGT
     ACG TTG ACA CAA CAA CCG ATG TAG CCG CTC GCG ACA GTC ATG GCA
      C   N   C   V   V   G   Y   I   G   E   R   C   Q   Y   R Afl II                       Pst I
     GAC CTT AAG TGG TGG GAA CTG CGC TGATAACCTGCA    3'
     CTG GAA TTC ACC ACC CTT GAC GCG ACTATTGG        5'
      D   L   K   W   W   E   L   R  (STOP)
```

FIG. 2A

C2, 35 mer ;  5' CATGACGGCTACTGCCTGCACGACGGCGTATGCAT 3'

C3, 29 mer ;  5' GTACATCGAAGCACTGGACAAATACGCGT 3'

C4, 39 mer, ;  5' GCAACTGTGTTGTTGGCTACATCGGCGAGCGCTGTCAGT 3'

C5, 41 mer ;  5' ACCGTGACCTTAAGTGGTGGGAACTGCGCTGATAACCTGCA 3'

N1, 29 mer ;  5' GGTTATCAGCGCAGTTCCCACCACTTAAG 3'

N2, 38 mer ;  5' GTCACGGTACTGACAGCGCTCGCCGATGTAGCCAACAA 3'

N3, 29 mer ;  5' CACAGTTGCACGCGTATTTGTCCAGTGCT 3'

N4, 36 mer ;  5' TCGATGTACATGCATACGCCGTCGTGCAGGCAGTAG 3'

N5, 38 mer ;  5' CCGTCATGGCTCAGCGGGCATTCGGAGTCGCTGTTAAC 3'

FIG. 2B

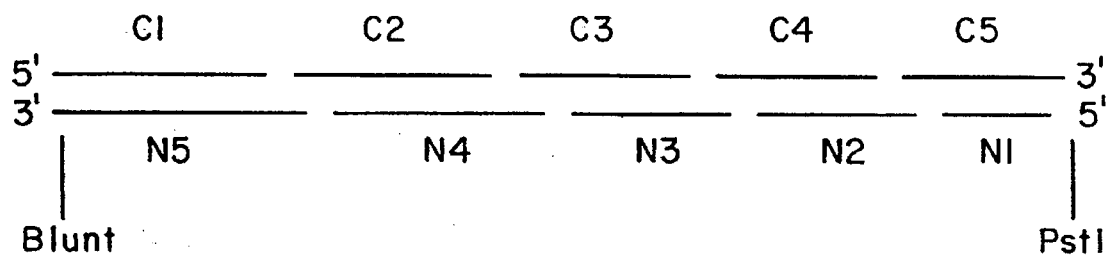

FIG. 5

BamH I     ┌──── Omp A leader sequence ────

5' GATCCAAAATT ATG AAA AAG ACA GCT ATC GCG ATT GCA GTG
3'       GTTTTAA TAC TTT TTC TGT CGA TAG CGC TAA CGT CAC

Nae I

GCA CTG GCT GGT TTC GCT ACC GTA GCG CAG GCC GGC
CGT GAC CGA CCA AAG CGA TGG CAT CGC GTC CGG CCG universal
                translation
Pst I ┌─ termination ─┐  ┌─Trp A transcription
                sequence CTG CAG CTT AAT TAA TTA AGC AGC CCG CCT AAT GAG
GAC GTC GAA TTA ATT AAT TCG TCG GGC GGA TTA CTC termination sequence┐ Xba I

CGG GCT TTT TTT      3'
GCC CGA AAA AAA AGA TC    5'

A B C D

A B C

A B C D E

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 174 base pairs
( B ) TYPE: nucleic acid
( C ) STRANDEDNESS: single
( D ) TOPOLOGY: linear ( i i ) MOLECULE TYPE: cDNA to mRNA (vi) ORIGINAL SOURCE:
  (A) ORGANISM: Homo sapiens (vii) IMMEDIATE SOURCE:
  (B) CLONE: EGF-nt seq (xi) SEQUENCE DESCRIPTION: SEQ ID NO:1:

```
GTTAACAGCG ACTCCGAATG CCCGCTGAGC CATGACGGCT ACTGCCTGCA CGACGGCGTA    60
TGCATGTACA TCGAAGCACT GGACAAATAC GCGTGCAACT GTGTTGTTGG CTACATCGGC   120
GAGCGCTGTC AGTACCGTGA CCTTAAGTGG TGGGAACTGC GCTGATAACC TGCA         174
```

(2) INFORMATION FOR SEQ ID NO:2:

(i) SEQUENCE CHARACTERISTICS:
    (A) LENGTH: 53 amino acids
    (B) TYPE: amino acid
    (C) STRANDEDNESS: single
    (D) TOPOLOGY: linear (ii) MOLECULE TYPE: protein (v) FRAGMENT TYPE: N-terminal (vi) ORIGINAL SOURCE:
    (A) ORGANISM: Homo sapiens (vii) IMMEDIATE SOURCE:
    (B) CLONE: EGF- AA SEQ (xi) SEQUENCE DESCRIPTION: SEQ ID NO:2:

```
Asn Ser Asp Ser Glu Cys Pro Leu Ser His Asp Gly Tyr Cys Leu His
 1               5                  10                      15

Asp Gly Val Cys Met Tyr Ile Glu Ala Leu Asp Lys Tyr Ala Cys Asn
             20              25                  30

Cys Val Val Gly Tyr Ile Gly Glu Arg Cys Gln Tyr Arg Asp Leu Lys
         35              40                  45

Trp Trp Glu Leu Arg
 50
```

(2) INFORMATION FOR SEQ ID NO:3:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: cDNA to mRNA (v) ORIGINAL SOURCE:
    (A) ORGANISM: Homo sapiens (vii) IMMEDIATE SOURCE:
    (B) CLONE: C1 PRIMER (xi) SEQUENCE DESCRIPTION: SEQ ID NO:3:

```
GTTAACAGCG ACTCCGAATG CCCGCTGAGC    30
```

(2) INFORMATION FOR SEQ ID NO:4:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: cDNA to mRNA (v) ORIGINAL SOURCE:

( A ) ORGANISM: Homo sapiens ( v i i ) IMMEDIATE SOURCE:
                    ( B ) CLONE: C2 PRIMER ( x i ) SEQUENCE DESCRIPTION: SEQ ID NO:4:

CATGACGGCT ACTGCCTGCA CGACGGCGTA TGCAT                                          3 5

( 2 ) INFORMATION FOR SEQ ID NO:5:

( i ) SEQUENCE CHARACTERISTICS:
                    ( A ) LENGTH: 29 base pairs
                    ( B ) TYPE: nucleic acid
                    ( C ) STRANDEDNESS: single
                    ( D ) TOPOLOGY: linear ( i i ) MOLECULE TYPE: cDNA to mRNA ( v i ) ORIGINAL SOURCE:
                    ( A ) ORGANISM: Homo sapiens ( v i i ) IMMEDIATE SOURCE:
                    ( B ) CLONE: C3 PRIMER ( x i ) SEQUENCE DESCRIPTION: SEQ ID NO:5:

GTACATCGAA GCACTGGACA AATACGCGT                                                 2 9

( 2 ) INFORMATION FOR SEQ ID NO:6:

( i ) SEQUENCE CHARACTERISTICS:
                    ( A ) LENGTH: 39 base pairs
                    ( B ) TYPE: nucleic acid
                    ( C ) STRANDEDNESS: single
                    ( D ) TOPOLOGY: linear ( i i ) MOLECULE TYPE: cDNA to mRNA ( v i ) ORIGINAL SOURCE:
                    ( A ) ORGANISM: Homo sapiens ( v i i ) IMMEDIATE SOURCE:
                    ( B ) CLONE: C4 PRIMER ( x i ) SEQUENCE DESCRIPTION: SEQ ID NO:6:

GCAACTGTGT TGTTGGCTAC ATCGGCGAGC GCTGTCAGT                                      3 9

( 2 ) INFORMATION FOR SEQ ID NO:7:

( i ) SEQUENCE CHARACTERISTICS:
                    ( A ) LENGTH: 41 base pairs
                    ( B ) TYPE: nucleic acid
                    ( C ) STRANDEDNESS: single
                    ( D ) TOPOLOGY: linear ( i i ) MOLECULE TYPE: cDNA to mRNA ( v i ) ORIGINAL SOURCE:
                    ( A ) ORGANISM: Homo sapiens ( v i i ) IMMEDIATE SOURCE:
                    ( B ) CLONE: C5 PRIMER ( x i ) SEQUENCE DESCRIPTION: SEQ ID NO:7:

ACCGTGACCT TAAGTGGTGG GAACTGCGCT GATAACCTGC A                                   4 1

( 2 ) INFORMATION FOR SEQ ID NO:8:

( i ) SEQUENCE CHARACTERISTICS:
                    ( A ) LENGTH: 29 base pairs
                    ( B ) TYPE: nucleic acid
                    ( C ) STRANDEDNESS: single
                    ( D ) TOPOLOGY: linear ( i i ) MOLECULE TYPE: cDNA to mRNA ( v i ) ORIGINAL SOURCE:
    ( A ) ORGANISM: Homo sapiens ( v i i ) IMMEDIATE SOURCE:
    ( B ) CLONE: N1 PRIMER ( x i ) SEQUENCE DESCRIPTION: SEQ ID NO:8:

GGTTATCAGC GCAGTTCCCA CCACTTAAG 29

( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: N2 PRIMER ( x i ) SEQUENCE DESCRIPTION: SEQ ID NO:9:

GTCACGGTAC TGACAGCGCT CGCCGATGTA GCCAACAA 38

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: N3 PRIMER ( x i ) SEQUENCE DESCRIPTION: SEQ ID NO:10:

CACAGTTGCA CGCGTATTTG TCCAGTGCT 29

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: N4 PRIMER ( x i ) SEQUENCE DESCRIPTION: SEQ ID NO:11:

TCGATGTACA TGCATACGCC GTCGTGCAGG CAGTAG 36

( 2 ) INFORMATION FOR SEQ ID NO:12:

( i ) SEQUENCE CHARACTERISTICS:

( A ) LENGTH: 38 base pairs
            ( B ) TYPE: nucleic acid
            ( C ) STRANDEDNESS: single
            ( D ) TOPOLOGY: linear ( i i ) MOLECULE TYPE: cDNA to mRNA ( v i ) ORIGINAL SOURCE:
            ( A ) ORGANISM: Homo sapiens ( v i i ) IMMEDIATE SOURCE:
            ( B ) CLONE: N5 PRIMER ( x i ) SEQUENCE DESCRIPTION: SEQ ID NO:12:

CCGTCATGGC TCAGCGGGCA TTCGGAGTCG CTGTTAAC                    38

( 2 ) INFORMATION FOR SEQ ID NO:13:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: cDNA to mRNA ( v i ) ORIGINAL SOURCE:
            ( A ) ORGANISM: Homo sapiens ( v i i ) IMMEDIATE SOURCE:
            ( B ) CLONE: OMP C1 PRIMER ( x i ) SEQUENCE DESCRIPTION: SEQ ID NO:13:

GATCCAAAAT TATGAAAAAG ACAGCTATCG CG                          32

( 2 ) INFORMATION FOR SEQ ID NO:14:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: cDNA to mRNA ( v i ) ORIGINAL SOURCE:
            ( A ) ORGANISM: Homo sapiens ( v i i ) IMMEDIATE SOURCE:
            ( B ) CLONE: OMP C2 PRIMER ( x i ) SEQUENCE DESCRIPTION: SEQ ID NO:14:

ATTGCAGTGG CACTGGCTGG TTTCGCTACC                             30

( 2 ) INFORMATION FOR SEQ ID NO:15:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: cDNA to mRNA ( v i ) ORIGINAL SOURCE:
            ( A ) ORGANISM: Homo sapiens ( v i i ) IMMEDIATE SOURCE:
            ( B ) CLONE: OMP C3 PRIMER ( x i ) SEQUENCE DESCRIPTION: SEQ ID NO:15:

GTAGCGCAGG CCGGCCTGCA GCTTAATTAA TT                          32

( 2 ) INFORMATION FOR SEQ ID NO:16:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: OMP C4 PRIMER ( x i ) SEQUENCE DESCRIPTION: SEQ ID NO:16:

```
AAGCAGCCCG CCTAATGAGC GGGCTTTTTT TT                                    32
```

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: OMP N1 PRIMER ( x i ) SEQUENCE DESCRIPTION: SEQ ID NO:17:

```
CTAGAAAAAA AAGCCCGCTC ATTAGGCGGG CT                                    32
```

( 2 ) INFORMATION FOR SEQ ID NO:18:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: OMP N2 PRIMER ( x i ) SEQUENCE DESCRIPTION: SEQ ID NO:18:

```
GCTTAATTAA TTAAGCTGCA GGCCGGCCTG CG                                    32
```

( 2 ) INFORMATION FOR SEQ ID NO:19:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: OMP N3 PRIMER ( x i ) SEQUENCE DESCRIPTION: SEQ ID NO:19:

CTACGGTAGC GAAACCAGCC AGTGCCACTG C    31

( 2 ) INFORMATION FOR SEQ ID NO:20:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: OMP N4 PRIMER ( x i ) SEQUENCE DESCRIPTION: SEQ ID NO:20:

AATCGCGATA GCTGTCTTTT TCATAATTTT G    31

GENE CODING HUMAN EPIDERMAL GROWTH FACTOR AND PROCESS FOR PREPARING THE SAME

BACKGROUND OF THE INVENTION

1. Field of the Invention

The present invention relates to a novel gene coding human epidermal growth factor and a process for preparing the same. Specifically, the present invention relates to a novel human epidermal growth factor gene and a process for preparing the same employing a recombinant expression vector therefor.

2. Description of the Prior Art

It is known that human epidermal growth factor (hereinafter referred to as 'hEGF') is a polypeptide hormone consisting of 53 amino acids and 3 disulfide bridges[see: Cohen, S., J. Biol. Chem., 237:1555–1562(1962); Savage, C. R., Jr. et al., J. Biol. Chem., 248:7669–7672(1973); Savage, C. R., Jr. et al., J. Biol. Chem., 247:7612–7621 (1972)], and that hEGF plays an important role on the growth control in mammalian cells, inter alia epidermal and epithelial cells on molecular level[see: Sporn, M. B. et al., Nature (London), 313:745–747(1985); Sporn, M. B. et al., N. Engl. J. Med., 303:878–880(1980)] and the treatment of injury [see: Buckley, A. et al., Proc. Natl. Acad. Sci., USA, 82: 7340–7344(1985)]. Further, it has been reported that the hEGF can be applied in the treatment of a stomach ulcer, due to its ability to repress secretion of gastric acid into stomach [see: Gregory, H., J. Cell Sci. Suppl., 3: 11–17(1985)].

Under the circumstances, studies on the mass production of the hEGF has been actively carried out, since Starkey et al. reported the biochemical property of hEGF purified from human urine[see: Starkey, R. H. et al., Science, 189:800 (1975); Cohen, S. et al., Proc. Natl. Acad. Sci., USA, 72:1317(1975)]. Several researchers have accomplished cloning of hEGF gene by the recombinant DNA technology in a successful manner[see: Smith, J. et al., Nucleic Acids Res., 10:4467–4482(1982); Urdea, M. S . et al., Proc. Natl. Acad. Sci., USA, 80:7461–7465(1983); Oka, T. et al., Proc. Natl. Acad. Sci., USA, 82:7212–7216(1985)]. The prior art, however, has not described methods of producing hEGF to the level sufficient for industrial application, due to its low activity and productivity.

Accordingly, studies on the elevation of activity and productivity in hEGF manufacture have been carried out. These studies have concentrated on the preparation of the nucleotide sequence of hEGF gene efficient for its massive production and the expression vector whose regulatory function is strengthened.

SUMMARY OF THE INVENTION

In accordance with the present invention, the inventors synthesized a novel hEGF gene and a novel expression vector therefor which expresses high levels of hEGF and developed a process for preparing hEGF therefrom.

A primary object of the invention is, therefore, to provide a novel hEGF gene which is designed and chemically synthesized for the purpose of producing high levels of hEGF in E. coli .

Another object of the invention is to provide a novel process for preparing hEGF from a recombinant expression vector comprising said hEGF gene and a regulatory sequence.

BRIEF DESCRIPTION OF THE DRAWINGS

The above and the other objects and features of the present invention will become apparent from the following descriptions given in conjunction with the accompanying drawings, in which:

FIG. 1 depicts sequence of designed hEGF gene of the invention SEQ.ID.NO. 1 (DNA). and SEQ.ID.NO. 2(protein)

FIG. 2A depicts 10 oligonucleotides synthesized;

FIG. 2B depicts assembly pattern of synthesized 10 oligonucleotides of FIG. 2A;

FIG. 5 depicts the Omp A leader-universal translation termination-Trp A transcription termination sequence;

DETAILED DESCRIPTION OF THE INVENTION

Figure 3:
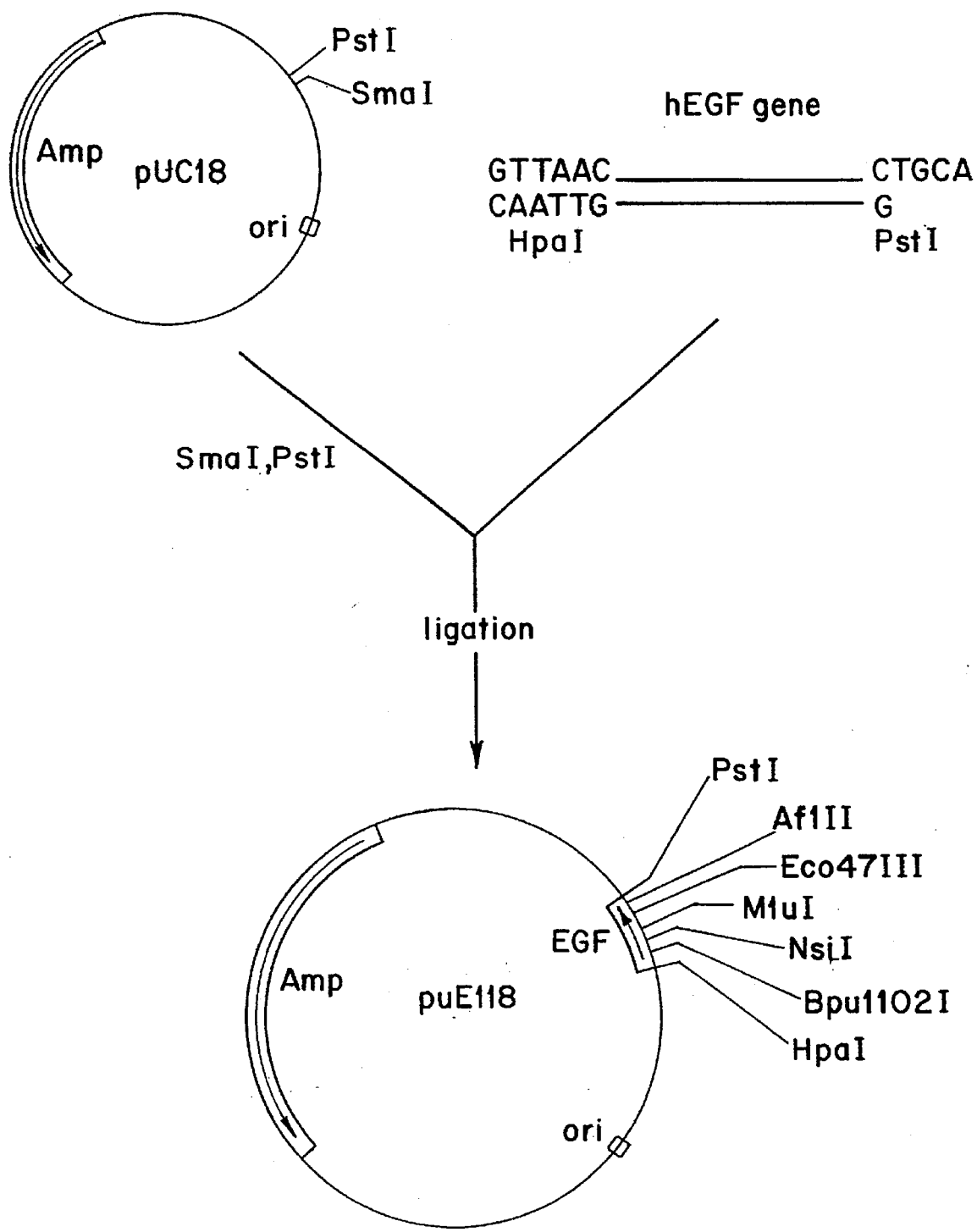
FIG. 3 depicts construction strategy of pUE118.

The inventors synthesized a hEGF gene designed to maximize expression of the gene which satisfies the following requirements: first, hEGF expressed therefrom shall be the same as natural human EGF in light of amino acid sequence and protein structure; secondly, nucleotide sequence shall be designed in consideration of the codons ubiquitous in E. coli; thirdly, the portion of secondary structure of mRNA transcribed therefrom shall be minimized; fourthly, many unique restriction sites shall be positioned as far apart as possible.

In this connection, the hEGF gene of the invention is designed, based on the previously known hEGF sequence in the art[See: Gregory, H., Nature, 257:325(1975)]. First of all, the inventors synthesized 10 complementary oligonucleotides by using automatic Nucleotide Synthesizer in accordance with solid-phase phosphate triester method[see: Narang, S. A., Synthesis and Applications of DNA and RNA, Academic Press, 1987]. To obtain the full hEGF gene, a shot-gun ligation method was employed.

The hEGF of the present invention contains the following restriction sites: HpaI at the 5' terminal, PstI at the 3' terminal and BpuI102I, NsiI, MluI, Eco47III and AflII within its internal sequence. Introduction of the hEGF gene to pUC18 which is a starting vector of the invention, produces the above 7 specific sites which exist as unique restriction sites in the recombinant vector. The fact that said unique sites are cleaved by their specific restriction enzymes and positioned at a regular interval, allows practical availability of the gene for mutagenesis induction, which assures high activity and stability of hEGF. Furthermore, the existence of HpaI restriction site at the 5' terminal allows production of intact hEGF free of fusion protein from the expression vector.

The hEGF gene of the invention was inserted into pUC18 digested with SmaI and PstI, and plasmid thus obtained was named pUE118. *E. coli* JM109 was transformed with pUE118 according to Hanahan's method[see: DNA Cloning Vol.I: A Practical Approach, IRL Press, 1985, pp 109–135]. This transformant was deposited with Korean Culture Collection of Microorganisms(KCCM) located in Department of Food Engineering, College of Eng., Yonsei University, Sodaemun-gu, Seoul 120–749, Korea on Apr. 9, 1993 in the name of *E. coli* DW/BT-2040(KCCM 10026).

On the other hand, it has been well known that the regulation of protein expression corresponding to the growth pattern of a microorganism is very important in the massive production of a protein. In this connection, a tac promoter [see: de Boer et al., DNA, 2:231–235(1983); Amann et al., Gene, 25:167–178(1983)] is introduced into the expression vector of the invention. Since the tac promoter has two continuous ribosome binding sites downstream from the tac promoter [see: Shine and Dalgarno, Proc. Natl. Acad. Sci., USA, 71:1342 (1974)], it initiates the translation of the hEGF gene efficiently.

For the accurate and efficient expression and secretion of hEGF, the expression vector of the invention employs the following sequences: (1) Omp A leader sequence[see: von Gabain, A. et al., Proc. Natl. Acad. Sci., USA, 80:653–657 (1983)]; (2) universal translation termination sequence[See: P. Singleton and D. Sainsbury, Dictionary of Microbiology and Molecular Biology, 2nd Ed., Wiley, 383, 1987]; and, (3) trp A transcription termination sequence[see: Christie, G. E. et al., Proc. Natl. Acad. Sci., USA, 78:418(1981)]. Further, the expression vector contains par site for the stability in *E. coli*[see: Austin and Abeles, J. Mol. Biol., 169:373–387 (1983)].

"Omp A leader-universal translation termination-trp A transcription termination sequence" is designed and synthesized to insert hEGF gene of the invention, which comprises restriction sites of BamHI at the 5' terminal and XbaI at the 3' terminal, and NaeI and PstI between the Omp A leader and universal translation termination sequence.

On the other hand, it has been known that secretion of the expressed protein is decreased when an ampicillin-resistant marker which codes β-lactamase, a secretory protein, is used to screen *E. coli* containing the vector comprising said marker. This is because the two proteins, i.e., interested protein and β-lactamase, compete in the course of secretion [see: A. Oka, et al., J. Mol. Biol., 147:217 (1981)]. A tetracycline-resistant marker coding intracellular protein, which brings about high secretion of expressed protein by avoiding said competition, is employed in the invention instead of the ampicillin-resistant marker. As a result, it is clearly guaranteed that the expression vector of the invention expresses and secretes hEGF in high levels, and is stable in *E. coli*.

A commercially available plasmid pDR540 is digested with PvuII and then ligated with XbaI linker. A double digestion with XbaI and BamHI is carried out. 2.4 kb of DNA fragment thus obtained is ligated with "Omp A leader-universal translation termination-Trp A transcription termination sequence"; and named pDT420.

Double digestion of pDT420 with NaeI and PstI produces a cleavage between Omp A leader and universal translation termination sequence; and, pUE118 carrying hEGF gene of the invention is digested with HpaI and PstI to obtain hEGF gene. Then, the obtained hEGF gene is ligated with the pDT420 and digested with NaeI and PstI, and the resultant is named pDE135.

Plasmid pUC19 known in the art is digested with DraI and EcoRI to obtain a 1.2 kb DNA fragment whose two ends are blunt-ended and cohesive for EcoRI, respectively; and, pBR322 is digested with AvaI and blunt-ended with Klenow's fragment, and digestion with EcoRI is followed to obtain 1.4 kb DNA fragment. The above 1.4 kb and 1.2 kb DNA fragments are ligated with $T_4$ DNA ligase, and is named pTC108. As a result, pTC108 comprises a tetracycline-resistant marker, a multiple cloning site and a replication origin of pUC19.

A par site is introduced for the stability of the expression vector in the transformant and exact separation of plasmids after cell division. Plasmid pTC108 is digested with EcoRI and SmaI. On the other hand, pSC101 is digested with AvaI to obtain 3.3 kb DNA fragment, which is blunt-ended with Klenow's fragment and then ligated with EcoRI linker followed by digestion with EcoRI. The 3.3 kb DNA fragment containing the sticky end of the EcoRI site is digested with HincII to obtain a 0.37 kb DNA fragment containing a par site. This 0.37 kb DNA fragment is ligated to the pTC108 and digested with EcoRI and SmaI by $T_4$ DNA ligase, and the ligated plasmid is named pTC226.

Plasmid pTC226 is digested with AflIII, blunt-ended with Klenow fragment and digested with XbaI in a serial manner to obtain 2.5 kb DNA fragment. On the other hand, pDE135 is digested with HindIII, blunt-ended with Klenow fragment and digested with XbaI in a serial manner to obtain a 0.45 kb DNA fragment. The 2.5 kb and 0.45 kb DNA fragments are ligated with $T_4$ DNA ligase, and the ligated plasmid is named pTE105.

*E. coli* JM101 is transformed with pTE105, and the transformant is deposited with Korean Culture Collection of Microorganisms(KCCM) located in Department of Food Engineering, College of Eng., Yonsei University, Sodaemun-gu, Seoul 120–749, Korea on Apr. 9, 1993 in the name of *E. coli* DW/BT-2042(KCCM 10027).

Transformants *E. coli* DW/BT-2042 are grown in LB media. The expression of hEGF therefrom is determined by 15% SDS-PAGE and Western blot analysis by employing commercially available hEGF(Amersham, ARN 5100, UK) as a standard. The amount of expressed hEGF is determined by hEGF receptor binding analysis employing the A431 cell line(ATCC CRL 1555). Culturing said transformant for 30 hrs gave 343.5 mg/L of hEGF, where most of the expressed hEGF was secreted out of cytosol.

The present inventors isolated hEGF from the culture, while reducing contamination of other cellular proteins and endotoxins, by employing a series of chromatographic purification methods, i.e., AmberChrom CG71 chromatography, Q-Sepharose anion exchange chromagraphy and reverse phase $C_{18}$ preparative HPLC. The purity of purified hEGF is determined by analytical HPLC in accordance with modified method of Hayashi et al's[see: Hayashi, T. et al., Anal. Sci., 3: 445–449(1987)].

The present invention is further illustrated in the following examples, which should not be taken to limit the scope of the invention.

EXAMPLE 1

Design of hEGF Gene

The hEGF gene was initially designed, based on the hEGF amino acid sequence and Grantham et al's study on the frequency of codon usage in *E. coli* [See: Grantham et al., Nucleic Acid Res., 9:243–274(1981)]. Then, a sequence which does not cause formation of secondary structure of mRNA transcribed therefrom was and examined to determine whether the gene contains codons ubiquitous in *E. coli* and causes formation of secondary structure of mRNA or not, by employing the PC-FOLD(Version 2.0) program[See: Turner, D. et al, Cold Spring Harbor Symp. Quant. Biol., 52:123(1987)]. The hEGF sequence thus designed carries the following two restriction sites to guarantee accurate insertion, isolation and manipulation of hEGF gene: HpaI at the 5' terminal; PstI down stream to the translational termination codon. The hEGF sequence further comprises many unique restriction sites at a regular basis as followings:

HpaI-22bp-Bpu1102I-39bp-NsiI-25bp-MluI-35bp-Eco47III-21bp-AflIII-32bp-PstI

The hEGF sequence designed in the invention is disclosed in FIG. 1, which shows positions of restriction sites: HpaI at the 5' terminal, PstI at the 3' terminal, and Bpu1102I, NsiI, MluI, Eco47III and AflIII.

EXAMPLE 2

Synthesis of Oligonucleotides

The hEGF gene designed in Example 1 was chemically synthesized. First of all, 10 oligonucleotides consisted of 29 mer to 41 mer were synthesized in a separate manner. They are disclosed in FIG. 2A: in this connection, C1(30 mer) SEQ. I.D. NO. 3, C2 (35mer) SEQ. I.D. NO. 4 , C3(29 mer), C4(39 mer)SEQ. I.D. NO. 6 and C5(41 mer)SEQ. I.D. NO. 7, oligonucleotides have the same sequence as that of mRNA transcribed from the corresponding hEGF sequence; and, N1(29 mer)SEQ. I.D. NO. 8, N2(38 mer)SEQ. I.D. NO. 9, N3(29 mer)SEQ. I.D. NO. 10, N4(36 mer)SEQ. I.D. NO. 11and N5 (38met)SEQ. I.D. NO. 12oligonucleotides were complementary to the C5, C4, C3, C2 and C1 oligonucleotides, respectively[See: FIG. 2B]. Each oligonucleotide was synthesized using an automatic Nucleotide Synthesizer(Pharmacia LKB Biotechnology, Uppsala, Sweden).

EXAMPLE 3

Isolation and Sequencing of Oligonucleotides

Oligonucleotides thus synthesized were separated on the silica matrix, through treatment with TTD solution (thiophenol/triethylamine/dioxane=1/2/2, v/v) and washing with methanol, ethanol and strong ammonia water in a serial manner. The solution containing oligonucleotide thus separated was subjected in strong ammonia water at 50° C. for 12 hrs to remove the protecting group. Concentration under vacuum was followed until a volume of 0.5 ml was achieved, together with removal of gas. The oligonucleotide solution thus concentrated was applied on a SEP-PAK cartridge(Waters Inc., MA, USA), and elution was made with acetonitrile/triethylamine solution to obtain partially purified oligonucleotide. Then, electrophoresis on 15% denatured polyacrylamide gel(TE-boric acid (pH 8.3) with 8M urea) was carried out and the location of oligonucleotide in the gel was determined by the irradiation of ultraviolet rays. The gel corresponding to oligonucleotide band was cut out, oligo-nucleotide was eletroeluted and salts were removed on SEP-PAK cartridge connected with injector by eluting with acetonitrile/triethlamine solution. The oligonucleotides thus isolated were labeled with $\gamma$-$^{32}$P-ATP by employing T$_4$ polynucleotide kinase(New England Biolabs., #201S, USA) and sequenced in accordance with Maxam & Gilbert's method[see: Maxam, A. M. & Gilbert, W., Proc. Natl. Acad. Sci., USA, 74:560–564(1977)].

EXAMPLE 4

Ligation of Oligonucleotides 100 pmole of each oligonucleotide prepared in Example 3, where all the oligonucleotides except for two oligonucleotides (C1 and N1) were phosphorylated at 5' terminal, were placed in Eppendorf tube with the addition of 40 μl 0.1M Tris-HCl(pH 7.5). Then, incubation was carried out at 100° C. for 3 min to denature the oligonucleotides, and renaturation was followed by lowering the temperature slowly. To the resultant were added 10 units of T$_4$ DNA ligase(New England Biolabs., #202S, USA) and ligation buffer solution, and incubated at 4° C. for 12 hr and at room temperature for 3 hrs, respectively. Then, 7% polyacrylamide gel electrophoresis and autoradiography were followed to determine the ligated hEGF sequence of the invention.

EXAMPLE 5

Construction of pUE118 and its Transformants pUC18 known in the art(see: Norrander, J. et al, Gene, 26:101(1985)) was digested with SmaI and PstI(New England Biolabs., #141S and #140S, MA, USA; all the restriction enzymes and linkers described hereinafter were purchased from New England Biolabs., MA, USA), and ligated with hEGF gene of the present invention. Ligation was easily performed, based on its nature of blunt 5' terminal and sticky 3' terminal in hEGF gene as designed. Recombinant vector thus obtained was named pUE118[see: FIG. 3].

Figure 4:
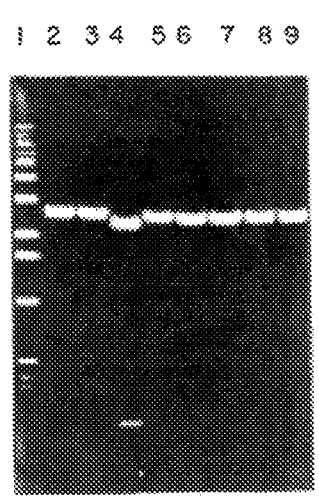
FIG. 4 is a photograph showing agarose gel electrophoresis pattern of pUE118 carrying hEGF gene digested with restriction enzymes.

Then, pUE118 were digested with HpaI, PstI, Bpu1102I, NsiI, MluI, Eco47III and AflIII, respectively, and electrophoresis of the gene fragments produced was carried out on 1% agarose gel. As disclosed in FIG. 4, the insertion of hEGF gene was carried out in an accurate manner and it was confirmed that single restriction site exists for each restriction enzyme. In FIG. 4, Lane 1 is the 1 kb ladder DNA (BRL, USA); Lanes 2 and 3 are pUE118 digested with HpaI and PstI, respectively; Lane 4 is pUE118 digested doubly with HpaI and PstI; and, Lanes 5–9 are pUE118 digested with Bpu1102I, NsiI, MluI, Eco47III and AflIII, respectively.

Competent *E. coli* JM109 was transformed with the pUE118; and *E. coli* JM109 thus transformed was deposited with the Korean Culture Center of Microorganisms(KCCM) in the name of *Escherichia coli*(DW/BT-2040) on Apr. 9, 1993 as deposition No. KCCM 10026.

EXAMPLE 6

Synthesis of "Omp A Leader-Universal Translation Termination-Trp A Transcription Termination Sequence"

Oligonucleotide comprising Omp A leader, universal translation termination and trp A transcription termination sequence designed to have several restriction sites as disclosed in FIG. 5. The oligonucleotide comprises restriction sites of BamHI at the 5' terminal end and XbaI at the 3' terminal, and NaeI and PstI between Omp A leader and universal translation termination sequence to assure that N-terminal amino acid sequence is exactly the same as the original protein and is free of additional amino acid sequences.

An Omp A leader-universal translation termination-Trp A transcription termination sequence was synthesized producing the following 8 oligonucleotides of 31 mer or 32 mer having the following sequences:

| | |
|---|---|
| 5' GATCCAAAATTATGAAAAAGACAGCTATCGCG | 3' (SEQ ID NO. 13 |
| 5' ATTGCAGTGGCACTGGCTGGTTTCGCTACC | 3' (SEQ ID NO: 14 |
| 5' GTAGCGCAGGCCGGCCTGCAGCTTAATTAATT | 3' SEQ ID NO: 15 |
| 5' AAGCAGCCCGCCTAATGAGCGGGCTTTTTTTT | 3' (SEQ ID NO. 16 |
| 5' CTAGAAAAAAAAGCCCGCTCATTAGGCGGGCT | 3' (SEQ ID NO: 17 |
| 5' GCTTAATTAATTAAGCTGCAGGCCGGCCTGCG | 3' SEQ ID NO. 18 |
| 5' CTACGGTAGCGAAACCAGCCAGTGCCACTGC | 3' SEQ ID NO. 19 |
| 5' AATCGCGATAGCTGTCTTTTTCATAATTTTG | 3' SEQ ID NO. 20 |

The oligonucleotides were synthesized an automatic Nucleotide Synthesizer(Pharmacia LKB Biotechnology, Uppsala, Sweden) in accordance with solid-phase phosphate triester methods[see: Narang, S. A., Synthesis and Applications of DNA and RNA, Academic Press, 1987].

In an analogy to Example 3, the synthesized oligonucleotides were separated from the silica matrix; removal of protecting group and concentration were followed; and isolation of oligonucleotides, labeling with $\gamma$-$^{32}$P-ATP, denaturation and renaturation, and ligation of oligonucleotides were performed.

EXAMPLE 7

Construction of Plasmid pDT420

Figure 6:
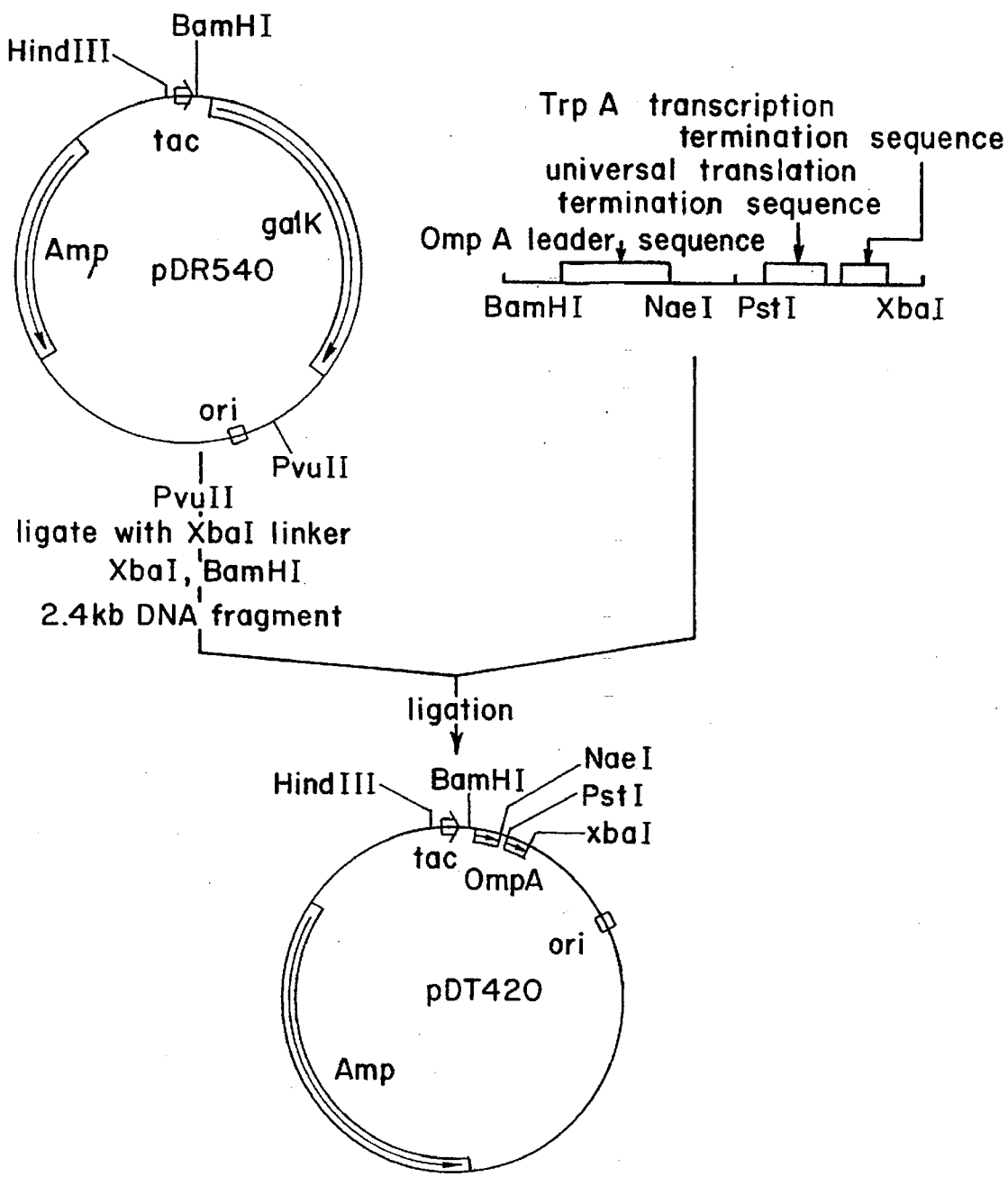
FIG. 6 depicts construction strategy of pDT420.

Plasmid pDR540(Pharmacia LKB Biotechnology, #27-4928-01, Upssala, Sweden) was digested with PvuII(#1032), ligated with XbaI linker and digested with XbaI(#145S) and BamHI (#136S) to obtain a 2.4 kb DNA fragment. Said fragment was isolated from the gel after electrophoresis of the digested fragments by employing Geneclean II DNA elution kit(BIO 101 Inc., CA, USA), and ligated with "Omp A leader-universal translation termination-Trp A transcription termination sequence" prepared in Example 6 by $T_4$ DNA ligase(#202S). E. coli JM101 was transformed with the ligated DNA according to Hanahan's method[see: DNA Cloning Vol.I; A Practical Approach, IRL Press, 109–135 (1985)]. From the transformants, recombinant plasmid was isolated and sequenced in accordance with Maxam and Gilbert's method to screen recombinant plasmid containing "OmpA leader-universal translation termination-Trp A transcription termination Sequence". The recombinant plasmid thus selected was named pDT420[see: FIG. 6].

EXAMPLE 8

Figure 7:
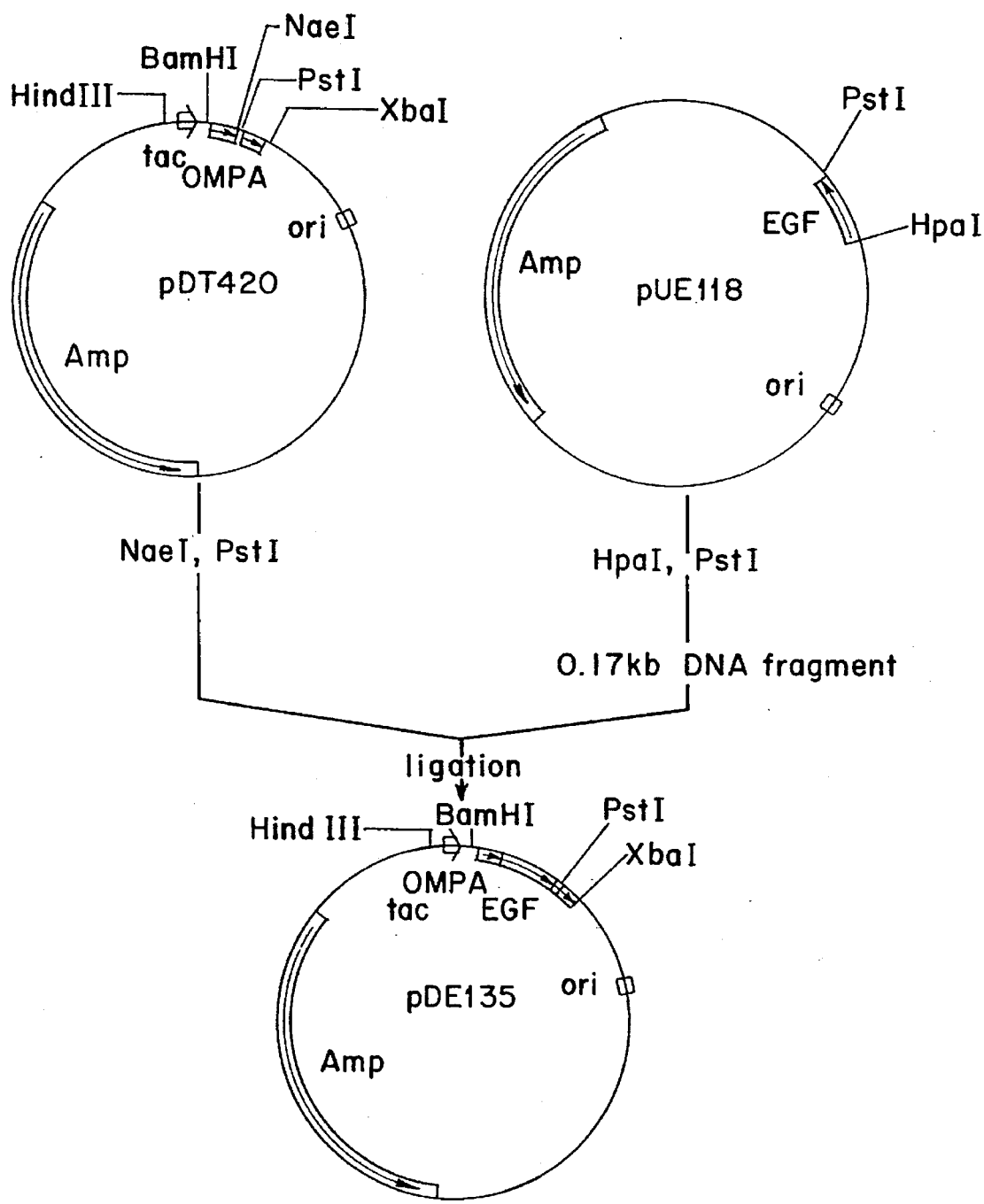
FIG. 7 depicts construction strategy of pDE135.

Construction of Expression Vector pDE135 and Determination of hEGF Expression Double digestion on plasmid pDT420 was made with NaeI (#190S) and PstI(#140S) to cleave the sequence between Omp A leader and universal translation termination sequence. On the other hand, plasmid pUE118 prepared in Example 5 was digested with HpaI(#105S) and PstI to obtain 0.17 kb hEGF gene. hEGF gene thus obtained was ligated with pDT420 and cleaved with NaeI and PstI, and the ligated DNA was transformed into E. coli JM101. From the transformants, recombinant plasmid was isolated by alkaline lysis method[Sambrook et al., Molecular Cloning, a laboratory manual, 2nd Ed., Cold Spring Harbor, 1989]. Referring to PstI and HindIII restriction enzyme map, recombinant plasmid containing hEGF gene between Omp A leader and universal translation termination sequence was selected and named pDE135[see: FIG. 7].

E. coli JM101 was transformed with pDE135, and the transformant was cultured in LB media(Luria-Bertani; Molecular Cloning/a laboratory manual, 2nd Ed., CSH, 1989). Then, expression of hEGF was investigated by SDS-PAGE and Western blot analysis. Expression of hEGF was determined by receptor binding assay(See: M. W. Rieman, Peptides, 8:877–885(1987)) employing A431 cell line (ATCC CRL 1555) using commercially available hEGF (Amersham, ARN 5100, UK) as a standard. hEGF was expressed with a yield of 10 mg/L after 30 hrs cultivation. Under the circumstance, the inventors assumed that the grounds of low efficiency of expression were: the biased transcriptional direction between ampicillin resistant marker and hEGF gene; competition of protein production; and, instability of the expression vector in the transformant. Accordingly, the inventors developed an improved hEGF expression cassette to solve the above confronted problems by employing a tetracycline resistant marker whose product was not secreted out of cytosol, instead of an ampicillin resistant marker.

EXAMPLE 9

Construction of Plasmid pTC108

Figure 8:
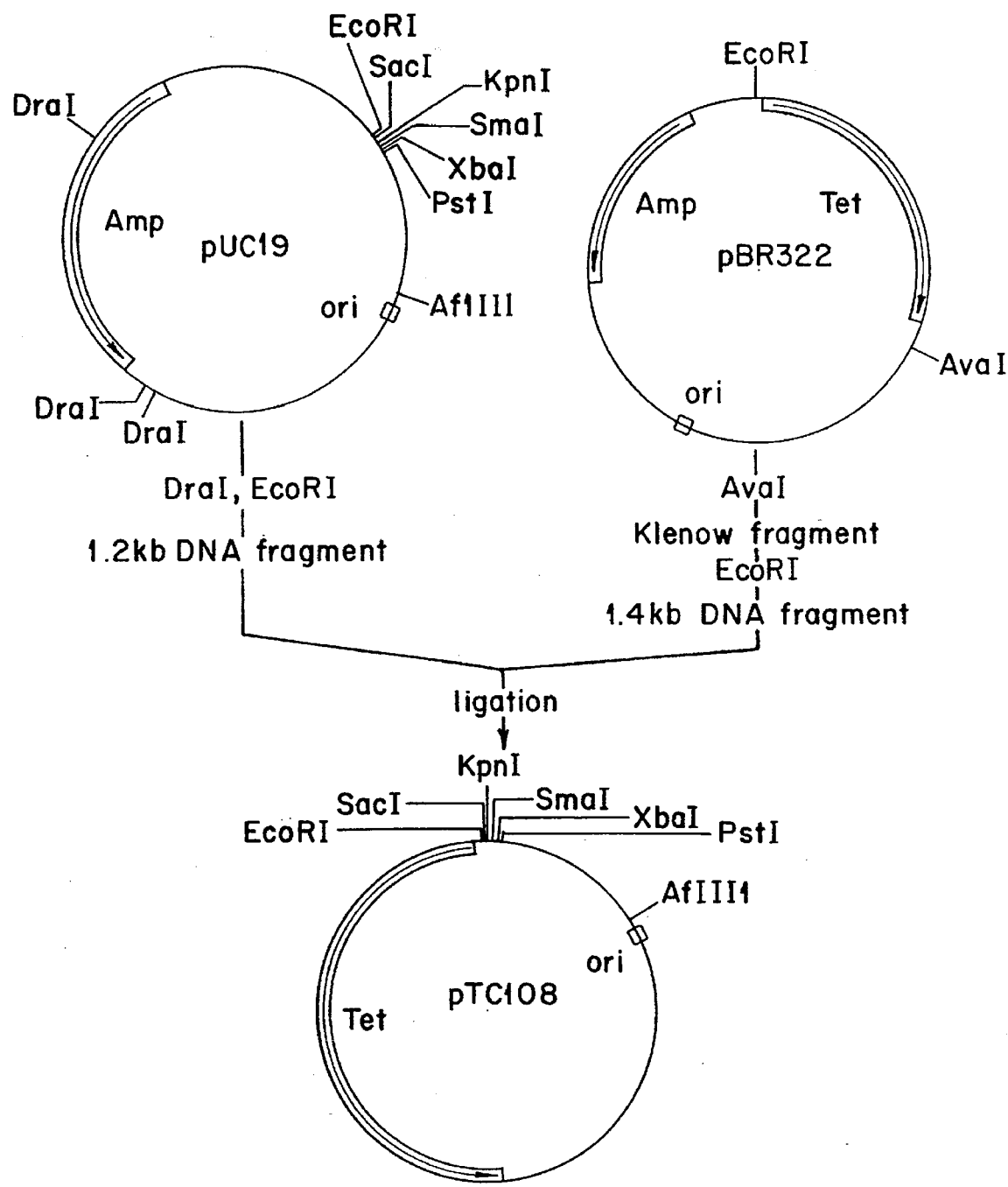
FIG. 8 depicts construction strategy of pTC108.

Plasmid pBR322(Bolivar, F. et al., Gene, 2:95–113 (1977)) was digested with AvaI(#152S), and manipulated with Klenow's fragment(#210S) to have blunt-end. Then, the resultant was digested with EcoRI and followed by electrophoresis on 0.8% agarose gel, and the 1.4 kb DNA fragment was obtained from the gel using Geneclean II DNA elution kit. On the other hand, pUC19(Yanish-Perron, C., et al., Gene, 33:103–119(1985)) was digested with DraI (#129S) and EcoRI to give a 1.2 kb DNA fragment. The 1.2 kb DNA fragment has a replication origin of pUc19 to maintain high efficiency of replication and multiple cloning site to ease gene manipulation. 1.4 kb and 1.2 kb DNA fragments thus obtained were ligated with $T_4$ DNA ligase, and E. coli JM101 was transformed with the ligated DNA fragment in accordance with Hanahan's method. From the transformants, recombinant plasmid was isolated by alkaline lysis. Referring to EcoRI and AflIII restriction enzyme map, recombinant plasmid containing replication origin of pUC19, multiple cloning site and tetracycline resistant marker was selected and named pTC108 [see: FIG. 8].

EXAMPLE 10

Construction of Plasmid pTC226

Figure 9:
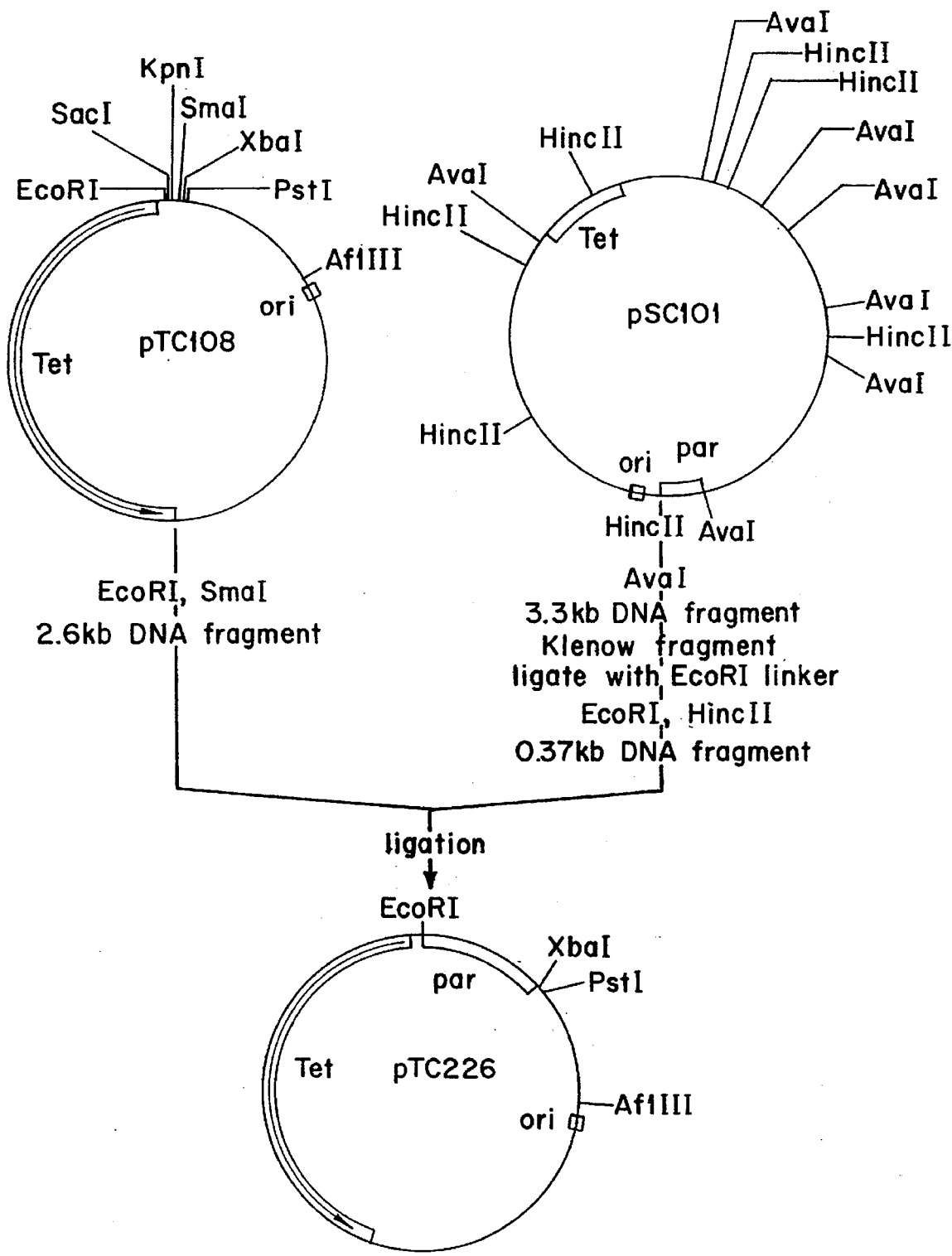
FIG. 9 depicts construction strategy of pTC226.

The inventors introduced par site for the stability of the expression vector in the transformant and easy separation of the plasmids after cell division. Plasmid pSC101(Cohen and Chang, Proc. Natl. Acad. Sci., USA, 70:1293–1297(1973); KCTC 11251) was digested with AvaI(#152S) and electrophoresed on 0.8% agarose gel. A 3.3 Kb DNA fragment was obtained therefrom by employing Geneclean II The DNA elution kit. DNA fragment thus obtained was manipulated with Klenow's fragment to produce blunt-end, ligated with EcoRI linker (#1020) and digested with EcoRI. The 3.3 kb DNA fragment containing sticky end of EcoRI site was digested with HincII(#103S) and electrophoresed on 0.8% agarose gel. A 0.37 kb DNA fragment containing a par site was obtained from electrophoresed gel by employing Geneclean II DNA elution kit. The obtained DNA fragment was ligated to pTC108 digested with EcoRI and SmaI (#141S) by the aid of $T_4$ DNA ligase, and $E.$ $coli$ JM101 was transformed with the ligated DNA fragment in accordance with Hanahan's method. From the transformants, recombinant plasmid was isolated by alkaline lysis. Referring to EcoRI and PstI restriction enzyme map, recombinant plasmid containing par site was selected and named pTC226 [see: FIG. 9].

EXAMPLE 11

Construction of Expression Vector pTE105

Figure 10:
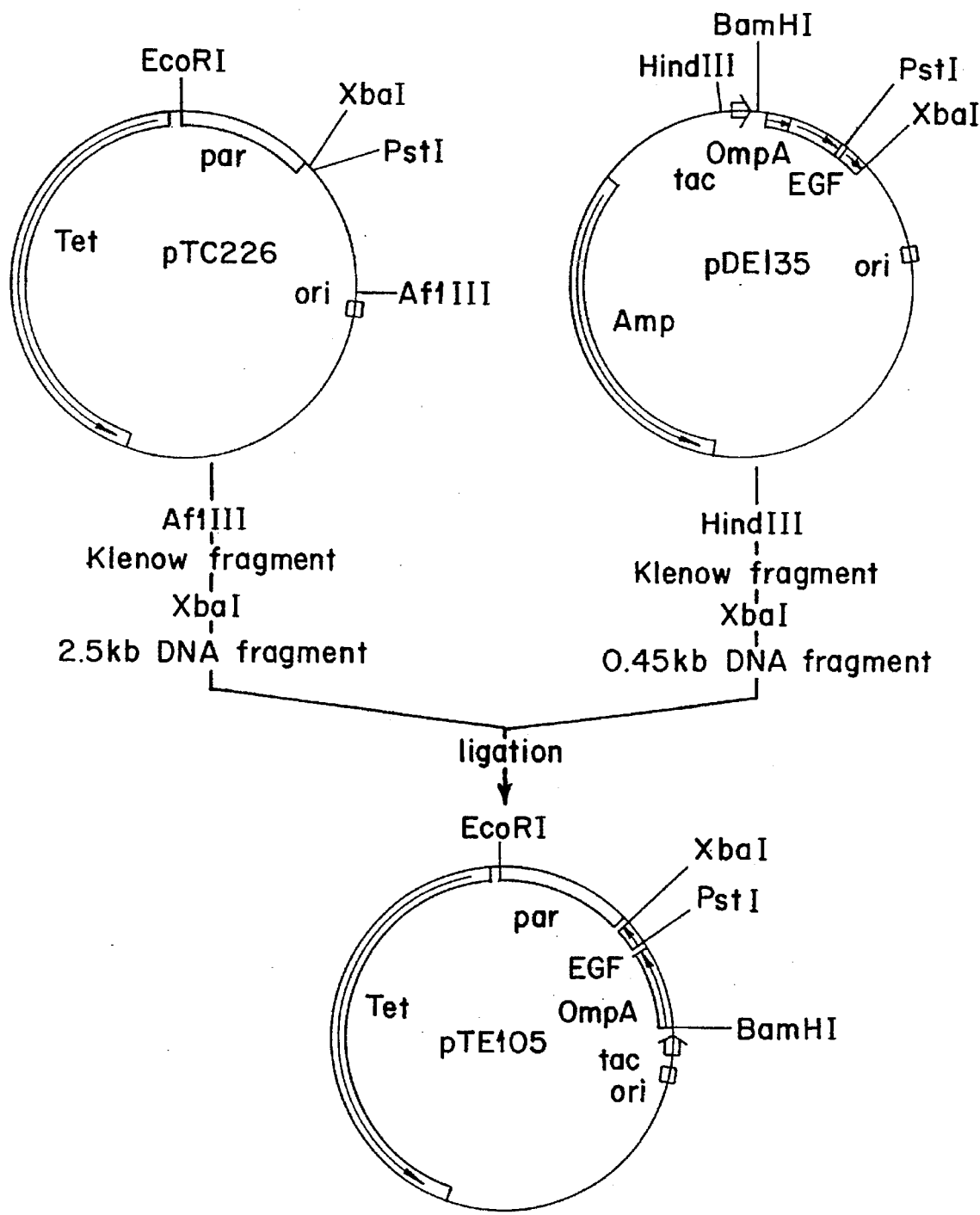
FIG. 10 depicts construction strategy of pTE105.

The inventors constructed a plasmid vector which is stable in $E.$ $coli$ and expresses high levels of hEGF, by inserting hEGF gene expression cassette of the pDE135 into pTC226 to have the same transcriptional direction. Plasmid pTC226 was digested with AflIII, manipulated with Klenow fragment to produce blunt-end, digested with XbaI(#145S) and electrophoresed on 0.8% agarose gel; and, 2.5 kb DNA fragment was obtained from electrophoresed gel by employing Geneclean II DNA elution kit. In the same manner, plasmid pDE135 was digested with HindIII(#104S), blunt-ended with Klenow fragment, digested with XbaI and electrophoresed on 1% agarose. A 0.45 kb DNA fragment was obtained from electrophoresed gel by employing Geneclean II DNA elution kit. Each isolated DNA fragment, i.e., 2.5 kb and 0.45 kb DNA fragments, was ligated with $T_4$ DNA ligase, and $E.$ $coli$ JM101 was transformed with the ligated DNA fragment in accordance with Hanahan's method. From the transformant, recombinant plasmid was isolated by alkaline lysis. Referring to restriction EcoRI and BamHI enzyme map, a recombinant plasmid containing tetracycline resistant marker, par site, and OmpA leader and hEGF gene was selected and named pTE105[see: FIG. 10]. $E.$ $coli$ JM101 transformed with pTE105 was named DW/BT-2042, and deposited with the Korean Culture Collection of Microorganisms(KCCM) on Apr. 9, 1993 as deposition No. KCCM 10027.

EXAMPLE 12

Expression of hEGF in Transformants

Figure 11A:
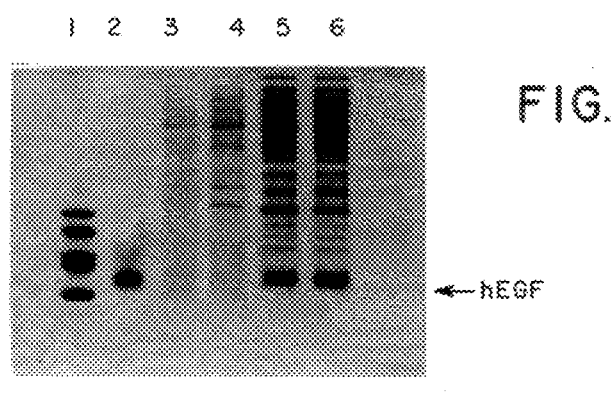
FIG. 11A is a photograph showing SDS-PAGE pattern of hEGF expressed in E. coli JM101 harboring pTE105.
Figure 11B:
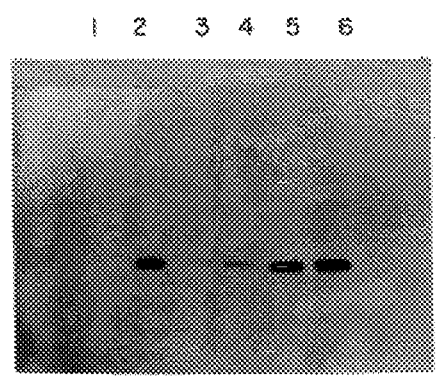
FIG. 11B is a photograph showing the Western blot analysis of hEGF expressed in E. coli JM101 harboring pTE105.

Transformant $E.$ $coli$ DW/BT-2042(KCCM 10027) was cultured in LB media for 5 hrs with the addition of isopropyl β-D-thio-galactoside(IPTG, Sigma I-6758) to the final concentration of 1 mM; and, cultures for 19 hrs and 25 hrs were collected and centrifuged respectively. The supernatants were electrophoresed on 15% polyacrylamide gel(see; H. Schagger et al., Anal. Biochem., 166:368–379(1987)) employing commercially available hEGF(Amersham, ARN 5100, UK) as a standard. FIG. 11A showed that molecular size of hEGF expressed was 6,000 dalton. Western blot analysis(W. N. Burnett, Anal. Biochem., 112:195–203 (1981)) was also carried out to confirm that the produced was hEGF[see: FIG. 11B]. In FIGS. 11A and 11B, Lane 1 is the molecular weight marker(Sigma, #MW-SDS-17S); Lane 2 is the standard hEGF; Lane 3 is the culture for 24 hrs without addition of IPTG; Lane 4 is the culture for 30 hrs without addition of IPTG; Lane 5 is the culture for 24 hrs with addition of IPTG; and, Lane 6 is the culture for 30 hrs with addition of IPTG. The amount of the hEGF in cultures for 24 hrs and 30 hrs were analyzed quantitatively by hEGF receptor binding assay; and disclosed in Table 1.

As clearly illustrated in Table 1, it was determined that: total hEGF amount of cultivation for 30 hrs was 343.5 mg/L and most of expressed hEGF was secreted out of cytosol.

TABLE 1

| sample | Incubation time | |
|---|---|---|
| | 24 hours | 30 hours |
| Periplasm | 10.5 mg/L | 9.4 mg/L |
| Culture | 213.8 mg/L | 334.1 mg/L |
| Total | 224.3 mg/L | 343.5 mg/L |

EXAMPLE 13

Mass Production of hEGF

Transformant $E.$ $coli$ DW/BT-2042(KCCM 10027) was cultured in 4 ml of LB media containing 0.5% glucose and 12.5 μg/ml of tetracycline at 37° C. for 11 hrs. 400 μl of the culture was inoculated on 100 ml of the same media and incubated for 11 hrs to obtain seed culture. 80 ml of seed culture was added to 2 L of media containing bactotrypton 10 g, yeast extract 20 g, $KH_2PO_4$ 3 g, $Na_2HPO_4 \cdot 8H_2O$ 4 g, $(NH_4)_2HPO_4$ 2.5 g, $CaCl_2 \cdot 2H_2O$ 0.01 g, Sigma antifoam A 1 ml, glucose 5 g and tetracycline 5 mg per 1 L, and incubated at 30° C. After 4 hrs incubation, IPTG was added to the final concentration of 1 mM for induction of hEGF and further incubation was carried out for 26 hrs.

EXAMPLE 14

Quantitative Assay of Produced hEGF

The amount of expressed hEGF was determined by receptor binding assay employing A431 cell line(ATCC CRL 1555), which is a modified method of Rieman's[see: Rieman, M. W., Peptides, 8:877–885(1987)]and DiAugustine's[see: DiAugustine, R. P., J. Biol. Chem., 260:2807–2811(1985)]. The A431 cells were mixed with DMEM medium containing calf serum, inoculated on Costa 24 well cell culture plate to $4 \times 10^5$ cells/well and incubated under 5% $CO_2$-atmosphere at 37° C. for 6 or 7 days. The medium was changed every other day. Then, removal of medium and washing with saline phosphate buffer were followed, and cells were immobilized by treatment of 10% formaldehyde for 10 min. After the removal of formaldehyde was carried out by washing with saline phosphate buffer, 250 μl of receptor binding buffer consisting of 1% BSA, 0.2% sodium azide and saline phosphate buffer was added to every well. A standard hEGF solution diluted to 0.01–20 ng/20 μl was added and $^{125}$I-EGF(Amersham, IM196, UK) diluted to 30,000 cpm/100 μl in a serial manner, and incubation with shaking at 100 rpm was followed for 2 hrs. Then, each well was rinsed with receptor binding buffer and bound cells thereon were separated from the well by the incubation with 250 μl of cell lysis solution consisting of 0.1N NaOH and 1% SDS. Radioactivity of $^{125}$I-EGF bound cells were determined with the aid of a γ-scintillation counter (Packard Cobra II, USA).

EXAMPLE 15

Purification of hEGF

2 L of culture prepared in Example 13 was centrifuged (Sorvall™ RC 28S, USA) at 8,000 rpm for 30 min. The supernatant was loaded on Amberchrom CG71(Tosohass Corp., USA) column(2.5×40 cm) preequilibrated with 20 mM Tris buffer(pH 8.0). The supernatant was washed with 1 L of the same buffer; and step elution was carried out with 500 ml of 20 mM Tris buffer(pH 8.0) containing 40% acetonitrile. Flow rate was controlled at 60 cm/hr in the course of loading, washing and elution. The eluted hEGF fraction was stored at 4° C.

350 ml of hEGF fraction obtained as above was loaded on Q-Sepharose FF(Pharmacia, USA) column(2.5×40 cm) pre-equilibrated with 20 mM Tris buffer(pH 8.0) and washed with 500 ml of the same buffer. Elution was made with a linear gradient of 0M to 0.5M NaCl in 20 mM Tris buffer(pH 8.0). In this connection, flow rate was controlled at 55 cm/hr during loading, washing and elution. 316.4 mg of hEGF was obtained with 80 to 85% of purity.

The hEGF fraction obtained as above was adjusted to a pH of 6.5 with 20% phosphate solution, and loaded on a $C_{18}$ reverse phase column(Waters Delta Prep 4000, USA, 8×100 mm) and followed by second $C_{18}$ reverse phase column(8× 100 mm). The $C_{18}$ reverse phase columns employed were preequilibrated with 10 mM phosphate buffer(pH6.5); and, the flow rate was controlled at 4 ml/min. The elution of hEGF was carried out with 10 mM phosphate buffer(pH 6.5, buffer A) and 10 mM phosphate buffer containing 70% acetonitrile(buffer B). 98% of purity was obtained at the retention time of 29 min. Table 2 illustrates HPLC chromatographic conditions for hEGF purification.

TABLE 2

| Retention time (min) | Flow rate (ml/min) | Buffer ratio (A/B, %) | Gradient type |
|---|---|---|---|
| 0 | 4 | 0/100 | — |
| 2 | 4 | 74/26 | linear |
| 20 | 4 | 72/28 | linear |
| 45 | 4 | 70/30 | linear |
| 70 | 4 | 66/44 | linear |
| 75 | 4 | 0/100 | linear |
| 85 | 4 | 0/100 | linear |

Figure 12:
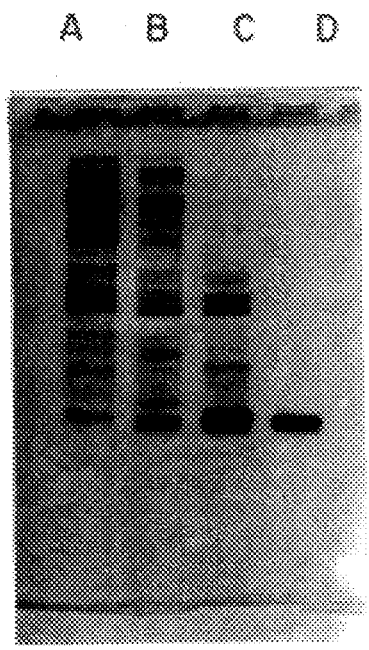
FIG. 12 is a photograph showing SDS-PAGE pattern of hEGF expressed from E. coli JM101 harboring pTE105 in each purification step.

The homogeneity of purified hEGF was determined by SDS-PAGE(Schagger. H. et al., Anal. Biochem., 166:368–379(1987))[see: FIG. 12]. In FIG. 12, Lane A is supernatant obtained by centrifugation of culture; Lane B is proteins isolated by Amberchrom CG71 chromatography; Lane C is proteins isolated by Q-Sepharose FF anion exchange chromatography; and, Lane D is purified hEGF by $C_{18}$ reverse phase HPLC.

The purification step of hEGF is summarized in Table 3.

TABLE 3

| Purification step | Total volume (ml) | Total hEGF (mg) | Total protein (mg) | Yield (%) | Specific activity (mg hEGF/ mg protein) |
|---|---|---|---|---|---|
| Culture | 2,000 | 582.1 | 5,490 | 100 | 0.106 |
| Amberchrom CG 71 | 350 | 436.5 | 997 | 74.9 | 0.438 |
| Q-Sepharose FF | 300 | 316.4 | 414 | 54.3 | 0.764 |
| $C_{18}$ HPLC | 240 | 282.3 | 285 | 48.4 | 0.990 |

Figure 13:
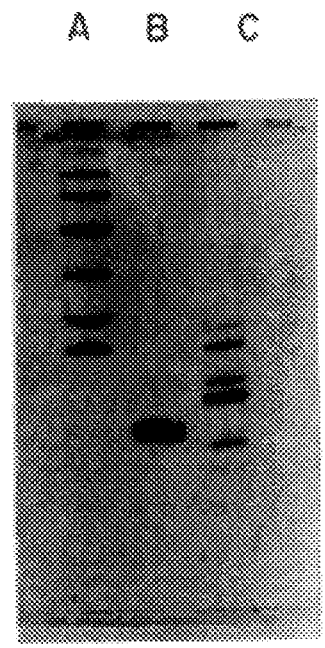
FIG. 13 is a photograph showing SDS-PAGE pattern of purified hEGF from E. coli JM101 harboring pTE105.

282.3 mg of purified hEGF was obtained with the yield of 48.4%. Protein concentration was determined by Bradford method(Bradford, M., Anal. Biochem., 72:248(1976)) employing protein quantitative kit(Biorad, #500-0006, USA). The molecular weight of purified hEGF was determined as 6,000 dalton by 15% SDS-PAGE analysis[see: FIG. 13]. In FIG. 13, Lane A is low molecular size weight marker(Biorad, #161-0304); Lane B is purified hEGF; and, Lane C is peptide marker(Sigma, #MW-SDS-17S).

Figure 14:
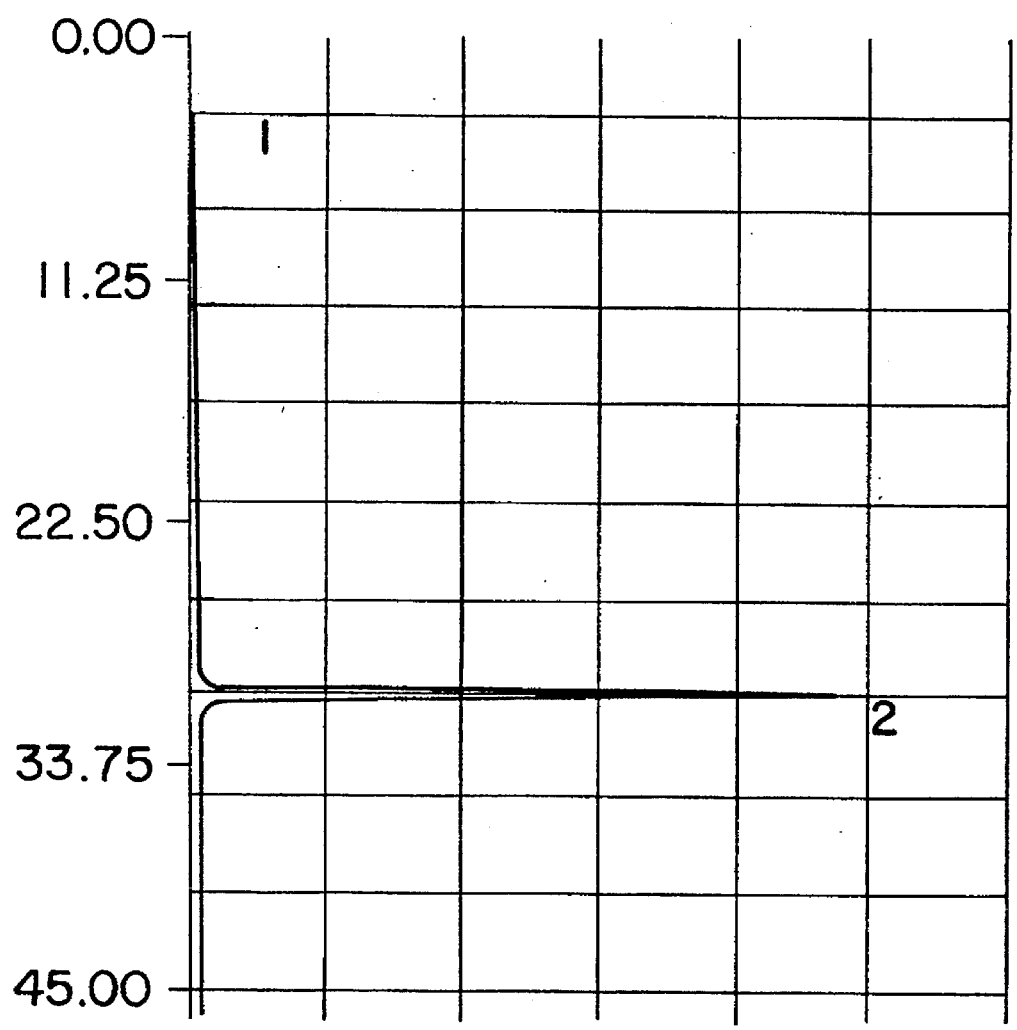
FIG. 14 is a chromatogram of purified hEGF by reverse phase HPLC.

The purity of purified hEGF was analysed in HPLC and represented in FIG. 14. As clearly disclosed in FIG. 14, it was determined that: the purity of hEGF was over 98% and degradation of C-terminal and oxidation of methionine did not occured.

Figure 15:
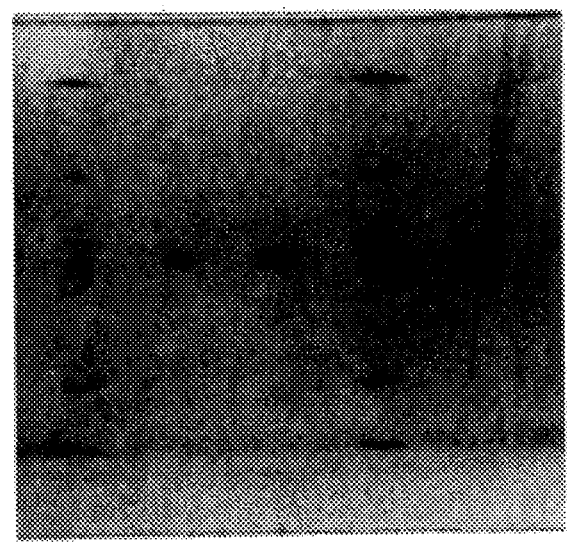
FIG. 15 is a photograph showing isoelectric focusing analysis of purified hEGF from E. coli JM101 harboring pTE105.

Finally, isoelectric focusing analysis was carried out for pI value determination in the pH range of 4 to 6 ampholite(see: Carfin, D. E., Methods Enzymol., 183:459–475 (1990)) and its result is shown in FIG. 15. In FIG. 15, Lanes A and D are low calibration isoelectric focusing analysis marker (Pharmacia, #17-0472-01, USA); Lanes B and C are 2 μg of purified hEGF; and, Lane E is 4 μg of purified hEGF. As shown in FIG. 15, it was determined that pI of the purified hEGF is 4.55, which is the same pI value of prior art hEGF.

EXAMPLE 16

Limulus Amebocyte Lysate Test

The purified hEGF was lyophilized and followed by Limulus Amebocyte Lysate test(Associates of Cape Code, USA). The result showed that the amount of endotoxin in hEGF was below 0.36 EU per 1 mg, which was extremely low. Accordingly, hEGF purification process of the invention was determined to be very efficient, while reducing contamination of other cellular protein and endotoxin.

What is claimed is:

1. An expression vector pTE105 for human epidermal growth factor comprising an expression cassette consisting of an Omp A leader sequence, a tetracycline-resistance marker, a par site, a translation termination sequence, and a transcription termination sequence and DNA encoding hEGF (SEQ ID NO:1), wherein the expression cassette is under transcriptional regulation by a tac promoter.

2. *E. coli* JM101(KCCM 10027) transformed with the expression vector of claim 1.

3. A process for preparing human epidermal growth factor (hEGF) from the culture of *E. coil* JM101(KCCM 10027) of claim 2, which comprises the steps of culturing said *E. coil* for a time and under conditions sufficient to induce hEGF in said culture, collecting the hEGF fraction from said culture, and purifying the hEGF fraction to obtain hEGF.

\* \* \* \* \*